United States Patent
Jadhav et al.

(10) Patent No.: US 11,833,148 B2
(45) Date of Patent: Dec. 5, 2023

(54) METHODS FOR TREATING OR LIMITING DEVELOPMENT OF CARDIOVASCULAR DISEASE-RELATED NEUROLOGICAL DISORDERS

(71) Applicant: ARIZONA BOARD OF REGENTS ON BEHALF OF THE UNIVERSITY OF ARIZONA, Tucson, AZ (US)

(72) Inventors: Sachin Suresh Jadhav, Tucson, AZ (US); Kevin Gaffney, Tucson, AZ (US); Kathleen E. Rodgers, Tucson, AZ (US); Maira Soto, Tucson, AZ (US)

(73) Assignee: Arizona Board of Regents on Behalf of the University of Arizona, Tuscon, AZ (US)

( * ) Notice: Subject to any disclaimer, the term of this patent is extended or adjusted under 35 U.S.C. 154(b) by 0 days.

(21) Appl. No.: 17/053,984

(22) PCT Filed: May 10, 2019

(86) PCT No.: PCT/US2019/031750
§ 371 (c)(1),
(2) Date: Nov. 9, 2020

(87) PCT Pub. No.: WO2019/217838
PCT Pub. Date: Nov. 14, 2019

(65) Prior Publication Data
US 2021/0283128 A1  Sep. 16, 2021

Related U.S. Application Data

(60) Provisional application No. 62/670,080, filed on May 11, 2018.

(51) Int. Cl.
*A61K 31/496* (2006.01)
*A61P 25/28* (2006.01)
(Continued)

(52) U.S. Cl.
CPC ........ *A61K 31/496* (2013.01); *A61K 31/4439* (2013.01); *A61P 9/12* (2018.01); *A61P 25/28* (2018.01)

(58) Field of Classification Search
CPC .. A61K 31/496; A61K 31/4439; A61K 31/16; A61K 31/18; A61K 31/4178;
(Continued)

(56) References Cited

U.S. PATENT DOCUMENTS 9,732,074 B2    8/2017    Petasis et al.
2016/0016946 A1  1/2016   Petasis et al.

FOREIGN PATENT DOCUMENTS

WO    WO-2009019531 A2 *   2/2009   ............ A61K 38/08
WO    WO 2014/145331         9/2018
WO    WO 2019/036267         2/2019

OTHER PUBLICATIONS

C.K. Firoz et al., An overview on the correlation of neurological disorders with cardiovascular disease, Saudi Journal of Biological Sciences (2015) 22, 19-23 (Year: 2015).*
(Continued)

*Primary Examiner* — Kortney L. Klinkel
*Assistant Examiner* — Padmaja S Rao
(74) *Attorney, Agent, or Firm* — Mark S. Cohen; Pearl Cohen Zedek Latzer Baratz LLP

(57) ABSTRACT

Disclosed herein are methods for treating or limiting development of cardiovascular disease-related neurological disorders by administering a compound of general formula (I), as defined herein.

(Continued)

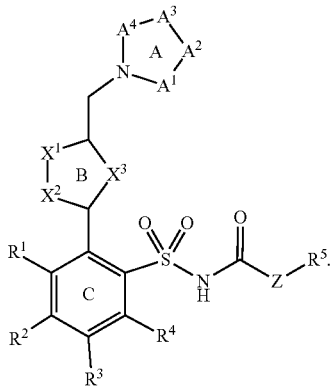

I

3 Claims, 2 Drawing Sheets

(51) Int. Cl.
*A61P 9/12* (2006.01)
*A61K 31/4439* (2006.01)

(58) Field of Classification Search
CPC .. C07D 213/44; C07D 213/52; C07D 417/06; C07D 401/06; A61P 9/12; A61P 25/28; A61P 9/00
See application file for complete search history.

(56) References Cited

OTHER PUBLICATIONS

Moazzami et al., Left Ventricular Hypertrophy and Remodeling and Risk of Cognitive Impairment and Dementia MESA (Multi-Ethnic Study of Atherosclerosis), Hypertension, Mar. 2018 (Year: 2018).*
International Search Report for PCT/US2019/031750 dated Jul. 1, 2019.
European Search Report for EP19799983.2 dated Apr. 14, 2022.

* cited by examiner

METHODS FOR TREATING OR LIMITING DEVELOPMENT OF CARDIOVASCULAR DISEASE-RELATED NEUROLOGICAL DISORDERS

CROSS REFERENCE

This application is a National Phase Application of PCT International Application No. PCT/US2019/031750, International Filing Date May 10, 2019, which claims priority to U.S. Provisional Patent Application Ser. No. 62/670,080, filed May 11, 2018, both of which are incorporated by reference herein in its their entirety.

BACKGROUND

Cardiovascular disease is a major risk factor for the development of neurological disorders, and thus methods for treating or limiting development of cardiovascular disease-related neurological disorders would be of value.

SUMMARY

In one aspect, the disclosure provides methods for treating or limiting development of a cardiovascular disease-related neurological disorder, comprising administering to a subject having a cardiovascular disease-related neurological disorder, or who is at risk of developing a neurological disorder, an amount effective to treat the cardiovascular disease-related neurological disorder of compound of general formula I as described herein.

In one embodiment, the cardiovascular disease comprises arterial hypertension and/or cardiac left-ventricular hypertrophy. In another embodiment, the cardiovascular disease-related neurologoical disorder comprises, cognitive decline, decline in executive function, dementia, Alzheimer's disease, neuroinflammation, and/or a neuroinflammatory disease.

DETAILED DESCRIPTION

Figure 1:
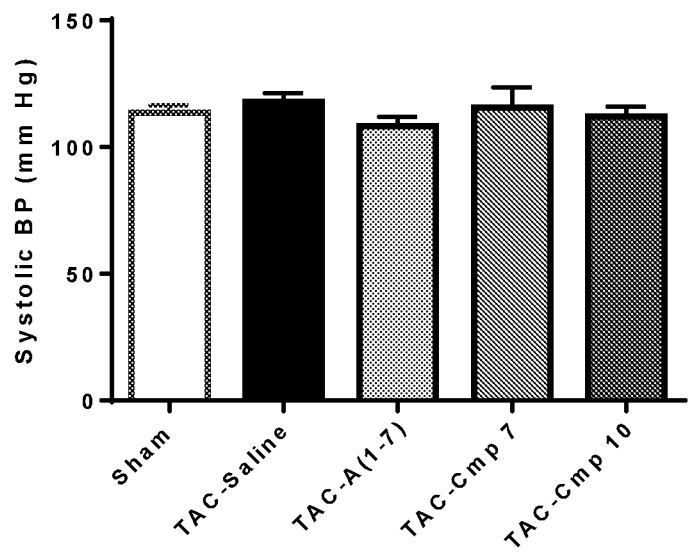
FIG. 1 is a graph showing the effects of treatment on systolic blood pressure. At approximately 5-6 weeks post-surgery, systolic blood pressure was measured 30 minutes after dosing by tail cuff. No significant differences between any groups were seen in systolic blood pressure.
Figure 2:
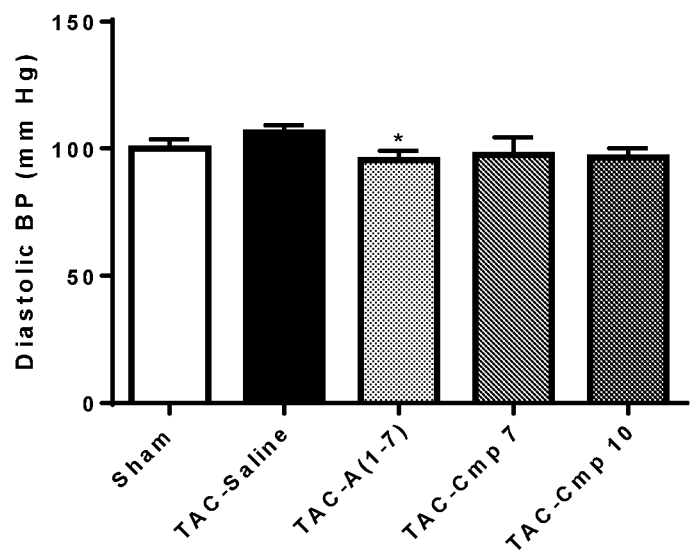
FIG. 2 is a graph showing the effects of treatment on diastolic blood pressure. At approximately 5-6 weeks post-surgery, diastolic blood pressure was measured 30 minutes after dosing by tail cuff. A (1-7) treatment significantly reduced diastolic blood pressure in TAC mice when compared to saline treated TAC mice. Compound 7 and Compound 10 had no significant effect on diastolic blood pressure. *=P≤0.05 as compared to saline treated TAC mice by t-test.
Figure 3:
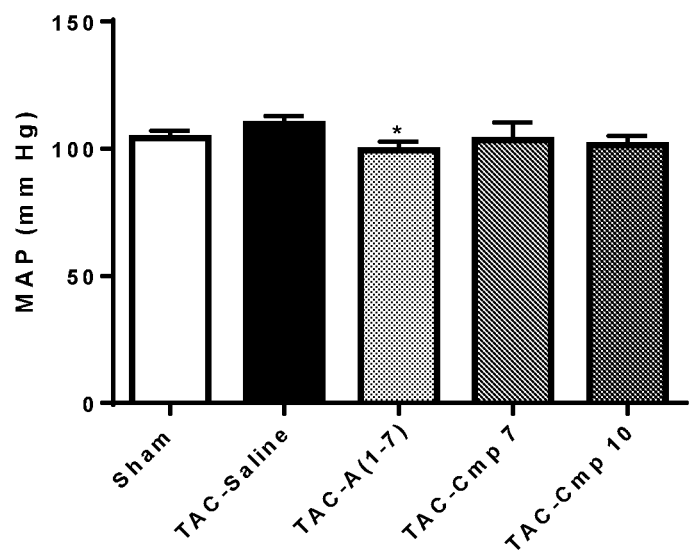
FIG. 3 is a graph showing the effects of treatment on mean arterial pressure (MAP). At approximately 5-6 weeks post-surgery, mean arterial pressure was measured 30 minutes after dosing by tail cuff. A (1-7) treatment significantly reduced mean arterial pressure in TAC mice when compared to saline treated TAC mice. Compound 7 and Compound 10 had no significant effect on mean arterial pressure. *=P≤0.05 as compared to saline treated TAC mice by t-test.
Figure 4:
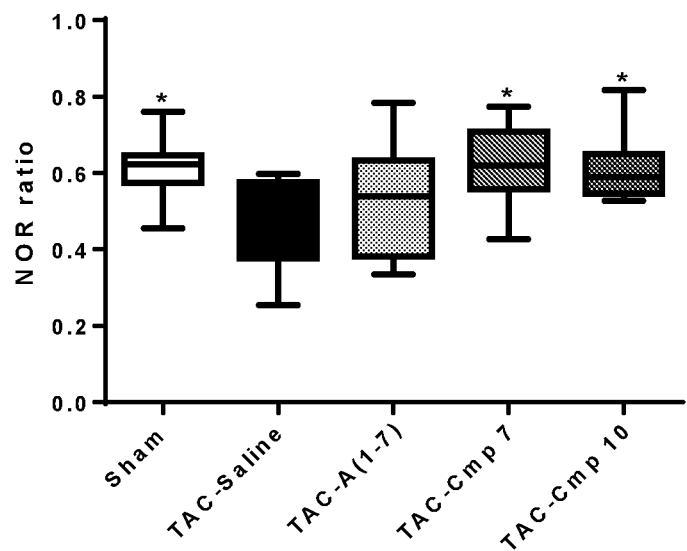
FIG. 4 is a graph showing the effects of treatment on novel object recognition (NOR). At 10 weeks post-surgery, the mice underwent NOR test to assess cognitive function. Saline treated TAC mice showed a decline in cognitive abilities whereas treatment with Compound 7 and Compound 10 restored NOR memory to sham levels. *=P≤0.05 as compared to saline treated TAC mice by t-test.

In one aspect, the disclosure provides methods for treating or limiting development of a cardiovascular disease-related neurological disorder, comprising administering to a subject having a cardiovascular disease-related neurological disorder, or who is at risk of developing a neurological disorder, an amount effective to treat the cardiovascular disease-related neurological disorder of compound of general formula I.

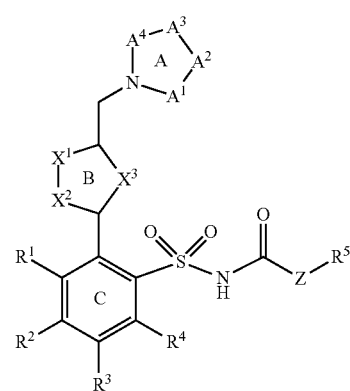

wherein:

ring A is a five-membered or six-membered heteroaryl or heterocyclyl ring containing either a combination of two non-adjacent nitrogen or oxygen atoms, or a combination of three or four nitrogen or oxygen atoms;

ring B is a five-membered or six-membered heteroaryl ring that contains at least one nitrogen atom;

ring C is an optionally substituted aryl ring;

$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, or —[C($R^a$)($R^d$)]$_n$— with n being 1 or 2;

$X^1$—$X^2$ is ($R^6$)C—N, N—C($R^6$), N—N, N—O, O—N, N—S or S—N;

$X^3$ is ($R^7$)C=C($R^8$), O, S, or N($R^9$);

Z is O, NH or a bond to $R^5$;

$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^a$ and $R^b$ can also join to form a ring of up to 6 atoms;

$R^c$ and $R^d$ are independently selected from a group consisting of hydrogen, alkyl, aryl, or heteroaryl, provided that $R^c$ and $R^d$ can also join to form a ring of up to 6 atoms;

$R^e$ is hydrogen, alkyl, aryl, heteroaryl, acyl, alkoxyacyl, aminoacyl, dialkylaminoacyl, or dialkylaminoacyl;

$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, bromo, iodo, cyano, hydroxy, amino, alkylamino, alkoxy, aryloxy, alkoxyalkyl, or aryloxyalkyl;

R[2] is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;

R[5] is alkyl, aryl, heteroaryl, hydroxyalkyl, carboxyalkyl, alkoxyalkyl, or aryloxyalkyl; and R[9] is hydrogen, alkyl, aryl, heteroaryl, acyl, alkoxyacyl, aminoacyl, dialkylaminoacyl, or dialkylaminoacyl.

or a pharmaceutically acceptable salt thereof.

The subject may be one having any suitable cardiovascular disease. In one embodiment, the subject has arterial hypertension. In another embodiment, the subject has cardiac left-ventricular hypertrophy. In a further embodiment, the subject has cardiac left-ventricular hypertrophy caused by arterial hypertension.

Any suitable subject may be treated using the methods of the disclosure, including but not limited to mammalian subjects, such as human subjects.

The compounds for use in the invention can be made, for example, by methods disclosed in U.S. Pat. No. 9,732,074.

The subject may be one having any suitable cardiovascular disease-related neurological disorder. In one embodiment, the subject has or is at risk of cognitive decline. In another embodiment, the subject has or is at risk of developing dementia. In another embodiment, the subject has or is at risk of developing Alzheimer's disease. In a further embodiment, the subject has or is at risk of developing neuroinflammation. In one embodiment, the subject has or is at risk of developing a neuroinflammatory disease.

As used herein, dementia means a group of symptoms associated with a decline in memory, reasoning or other thinking skills severe enough to reduce a person's ability to perform everyday activities, and may encompass subjects with Alzheimer's disease and other specific disorders.

As used herein, neuroinflammation means chronic inflammation of the central nervous system. It may be initiated in response to a variety of risk factors, including but not limited to infection, traumatic brain injury, spinal cord injury, toxic metabolites, or autoimmunity. Neuroinflammation may play a role in developing a variety of neurological diseases such as Alzheimer's disease, Parkinson's disease, and automimmune multiple sclerosis.

As used herein, neuroinflammatory disease means diseases caused by neuroinflammation, including but not limited to Alzheimer's disease, Parkinson's disease, amyotrophiC lateral sclerosis, systemic lupus erythematosus, and automimmune multiple sclerosis.

In one embodiment, ring A is selected from a group consisting of:

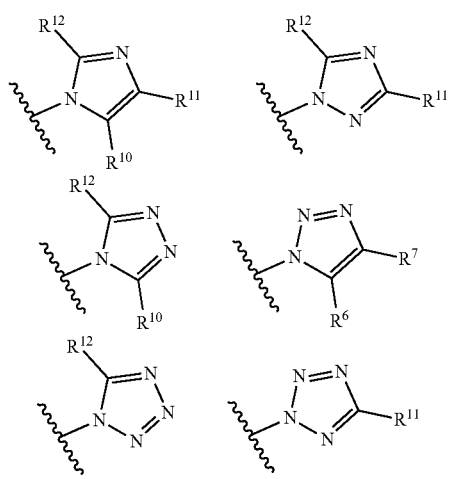

-continued

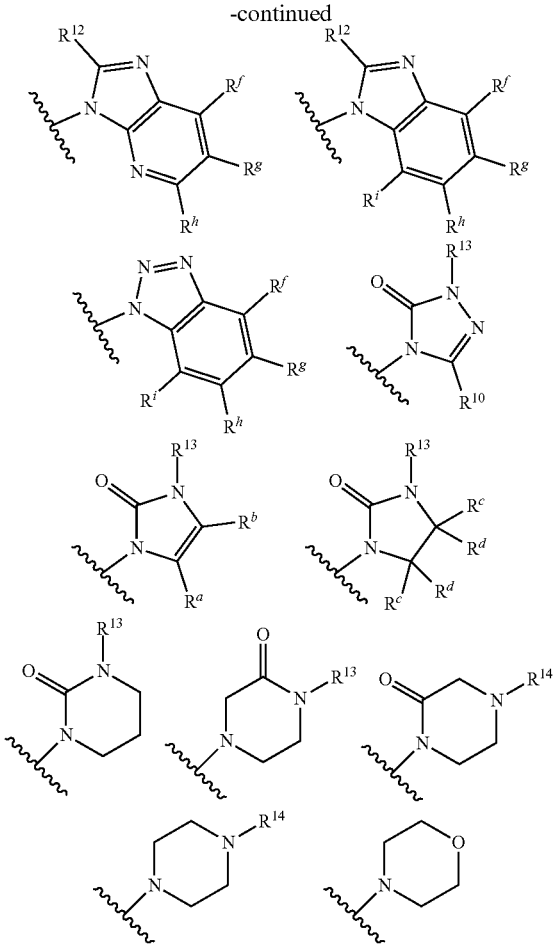

wherein:

R[10] and R[11] are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that R[10] and R[11] can also be joined to form a carbocyclic, heterocyclic, aryl or hetoaryl ring;

R[12] is hydrogen, alkyl, alkenyl, alkynyl, aryl, heteroaryl, halo, hydroxy, hydroxyalkyl, alkoxyalkyl, alkoxy, aryloxy, or acylamido;

R[13] is hydrogen, alkyl, aryl or heteroaryl;

R[14] is hydrogen, alkyl, aryl, heteroaryl, acyl, alkoxyacyl, aminoacyl, dialkylaminoacyl, or dialkylaminoacyl; and R[f], R[g], R[h], and R[i], are independently selected from a group consisting of hydrogen, alkyl, alkenyl, alkynyl, aryl, heteroaryl, arylmethyl, heteroarylmethyl, fluoro, bromo, iodo, hydroxy, amino, alkylamino, alkoxy, aryloxy, alkoxyalkyl, or aryloxyalkyl.

In another embodiment, ring B is selected from a group consisting of:

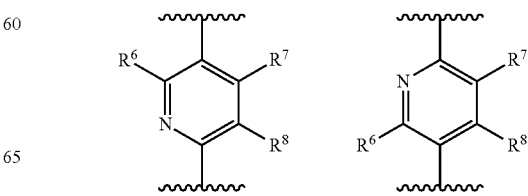

-continued
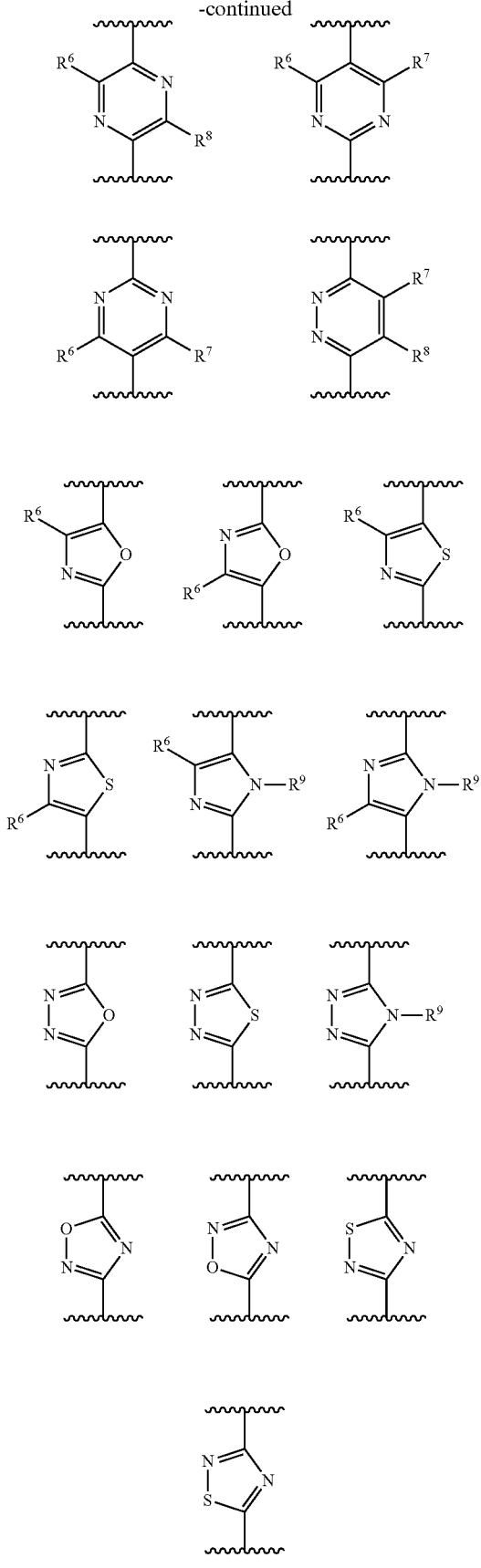
In a further embodiment, the compound has a general formula selected from a group consisting of:
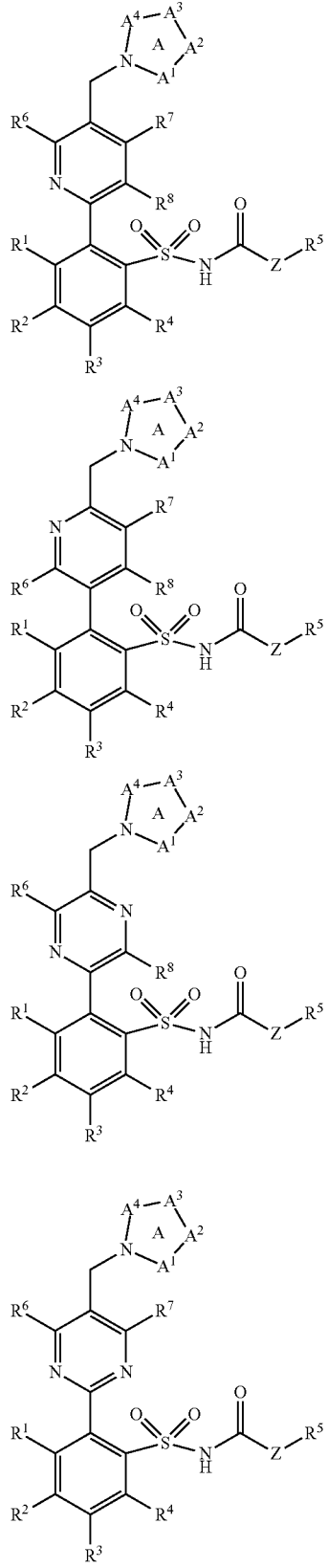

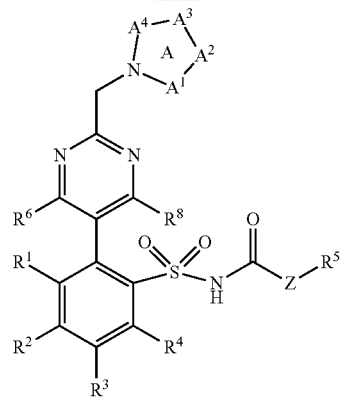
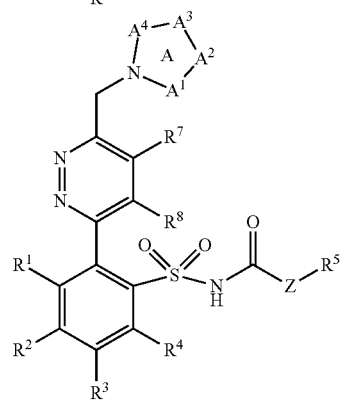
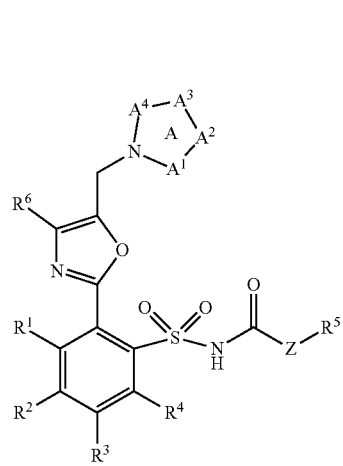
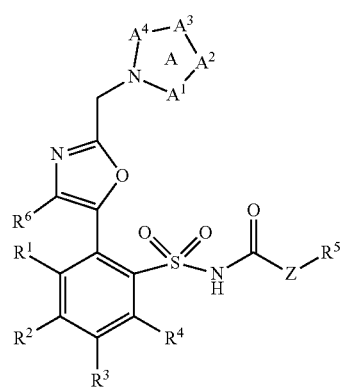
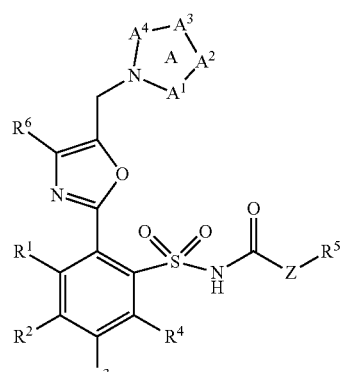
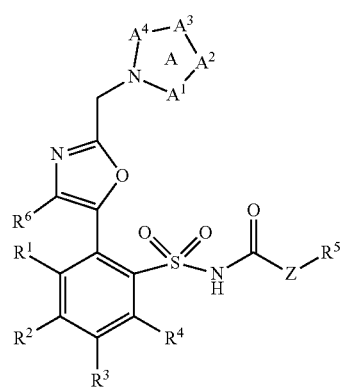

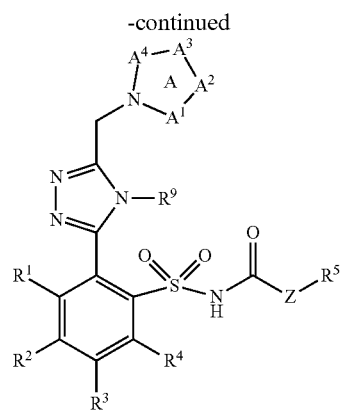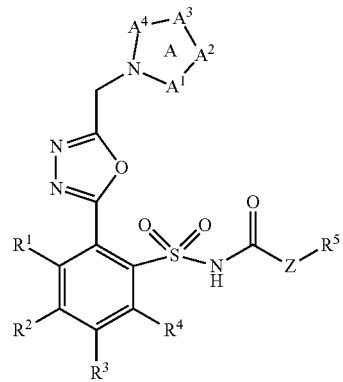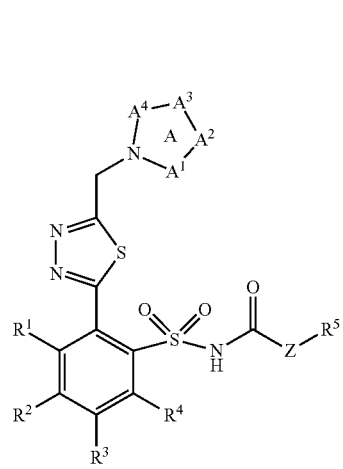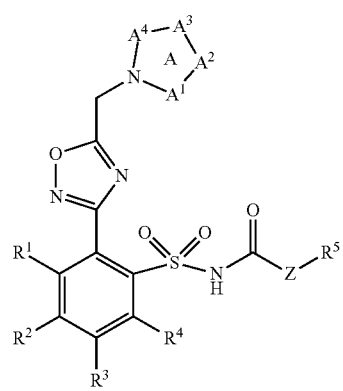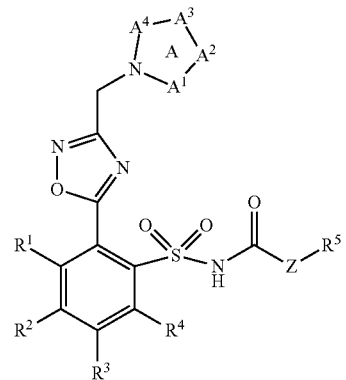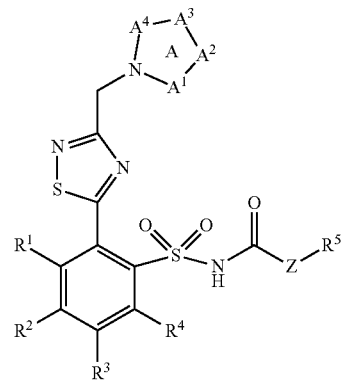
or a pharmaceutically acceptable salt thereof.

In another embodiment, the compound has a general formula selected from a group consisting of:
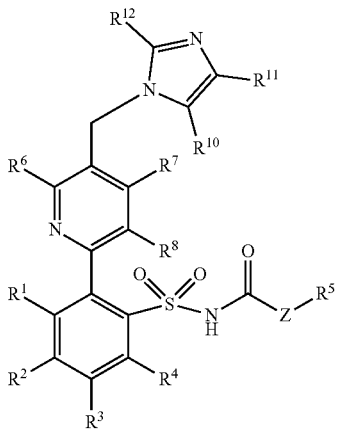
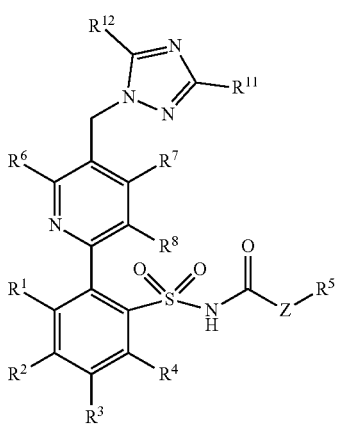
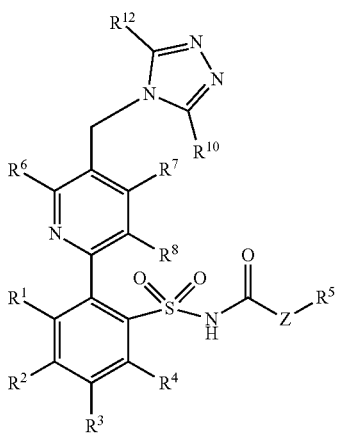
-continued
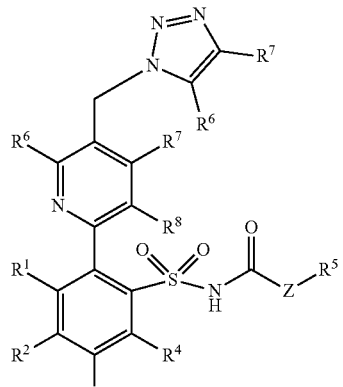
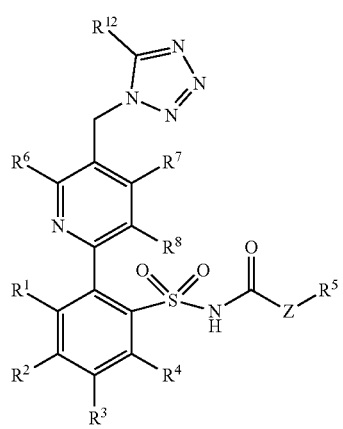
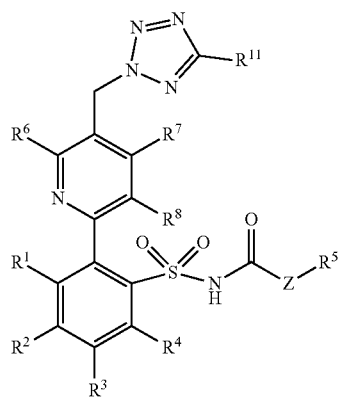
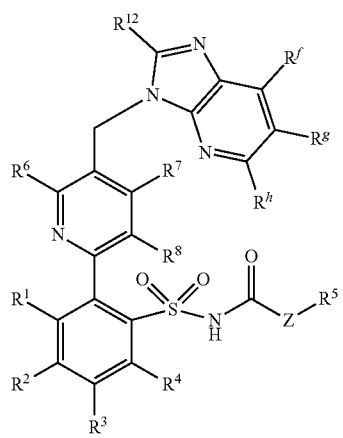

-continued
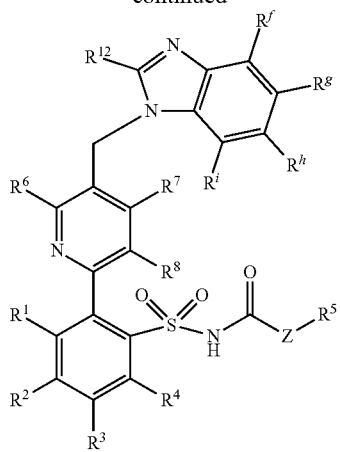
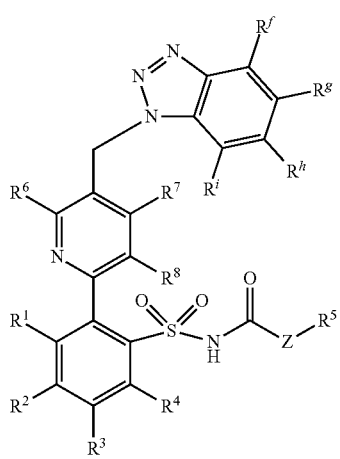
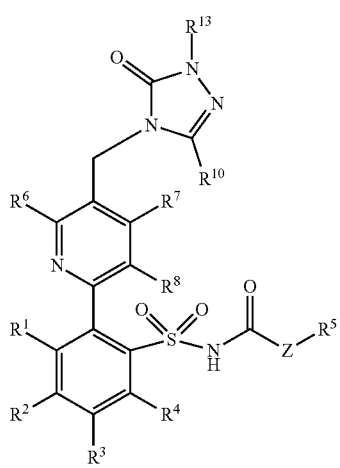
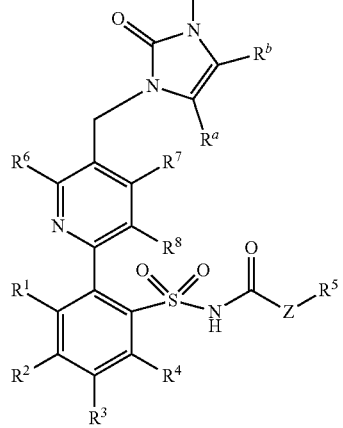
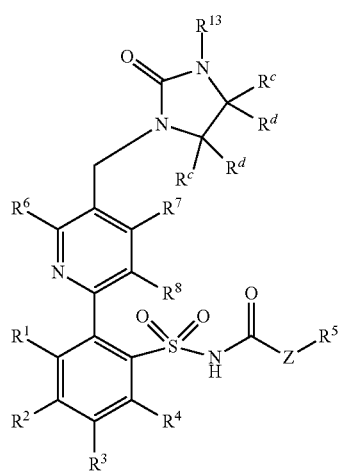
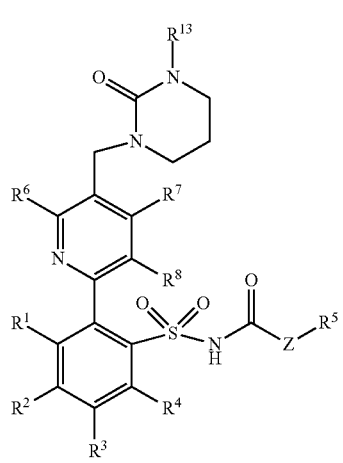

-continued
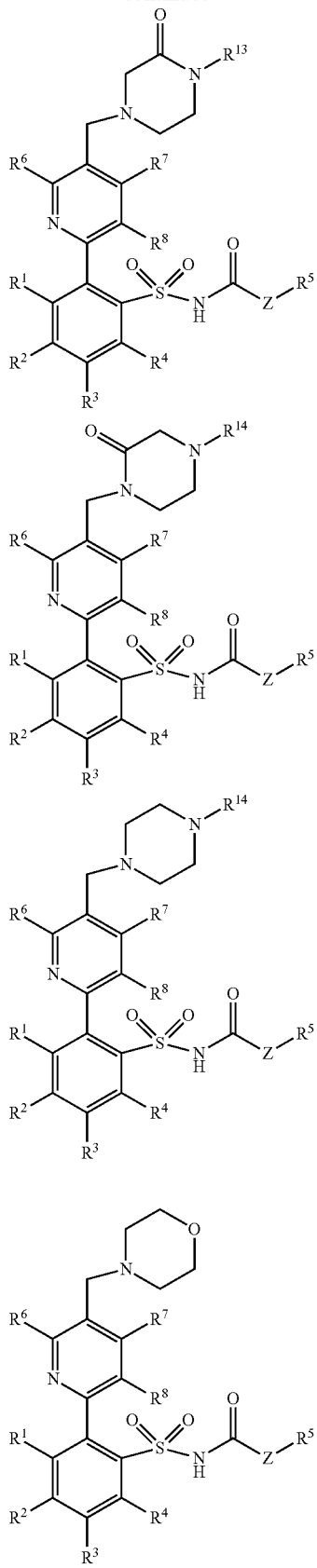
or a pharmaceutically acceptable salt thereof.
In one embodiment, the compound has a general formula selected from a group consisting of:
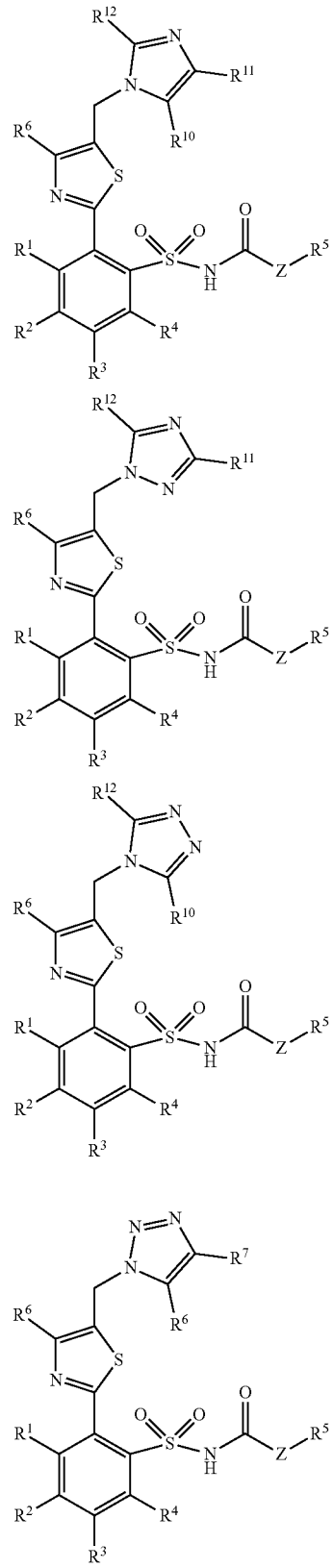

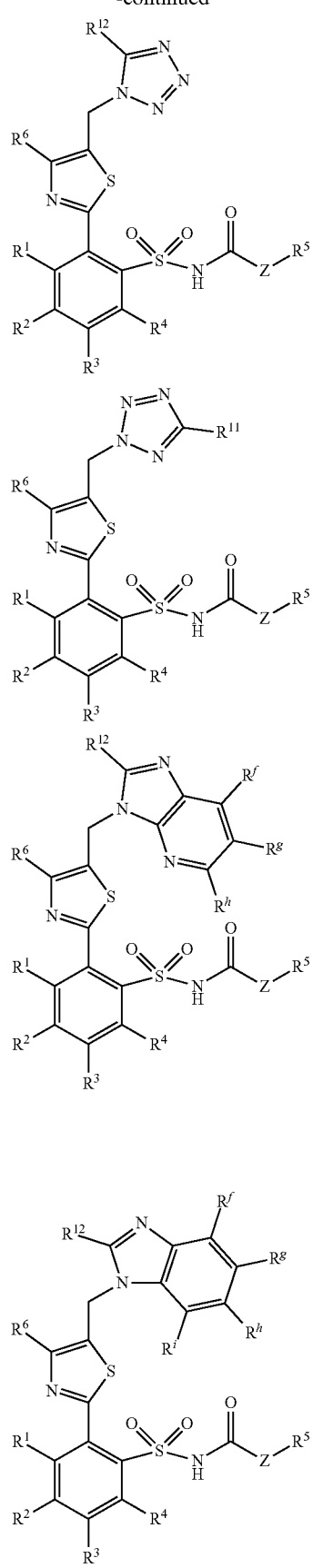
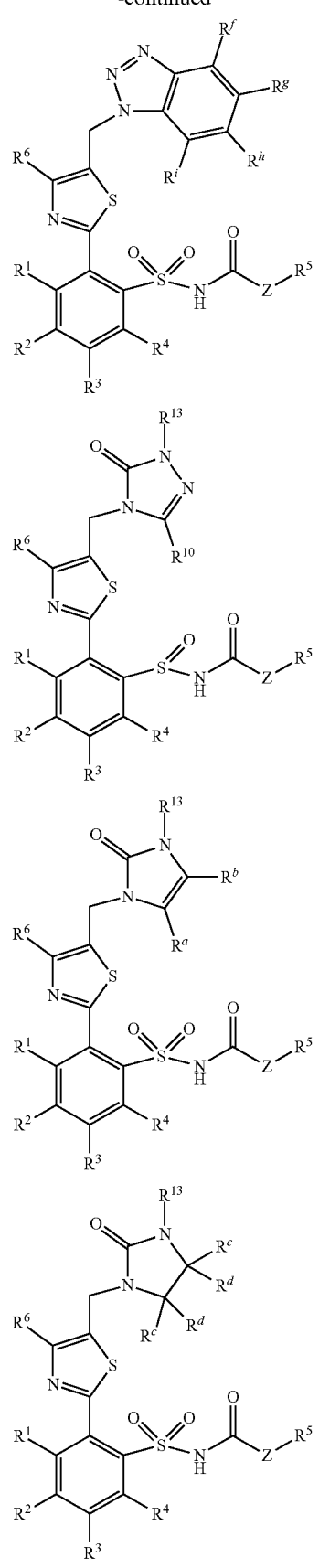

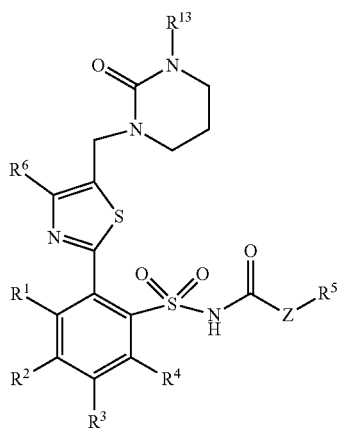
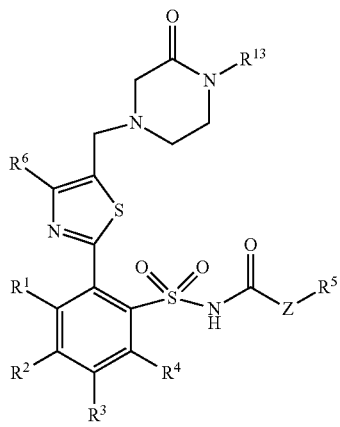
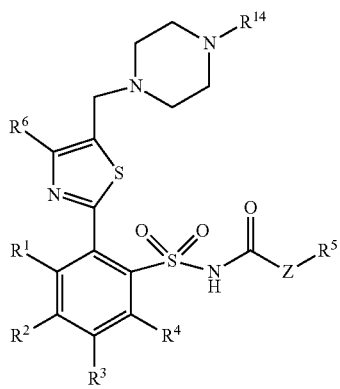
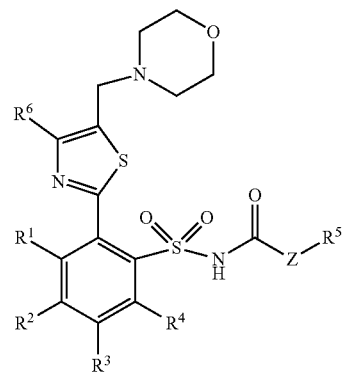
or a pharmaceutically acceptable salt thereof.
In another embodiment, the compound has a general formula 2a,b or 3a,b:
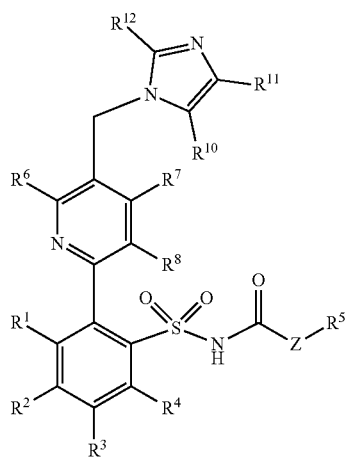
2a
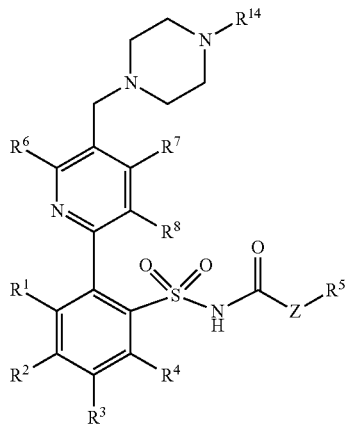
2b 3a
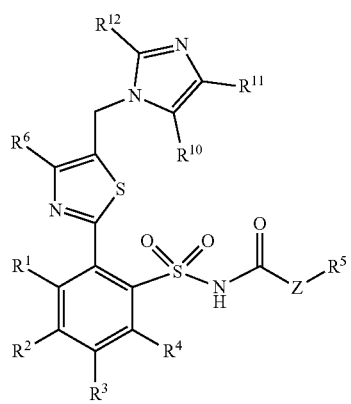
3b
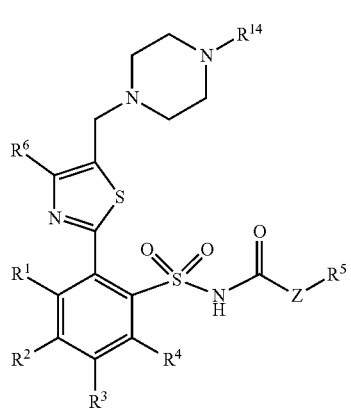
or a pharmaceutically acceptable salt thereof.
In a further embodiment, the the compound has the general formula 4a,b, 5a,b or 6a,b:
4a
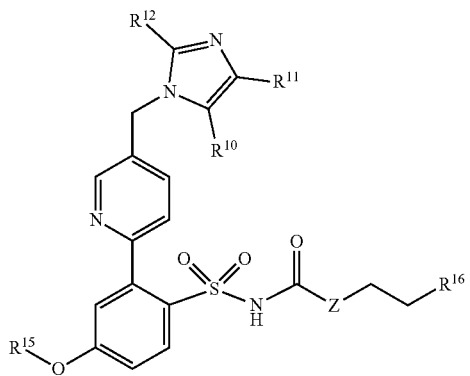
4b
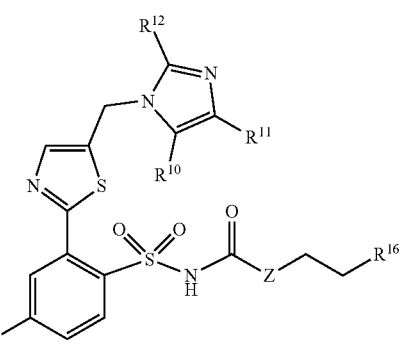
5a
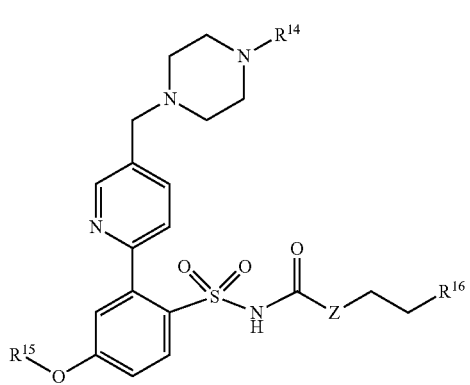
5b
6a
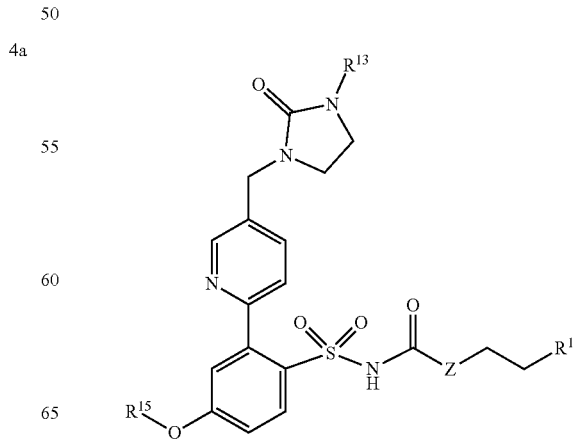

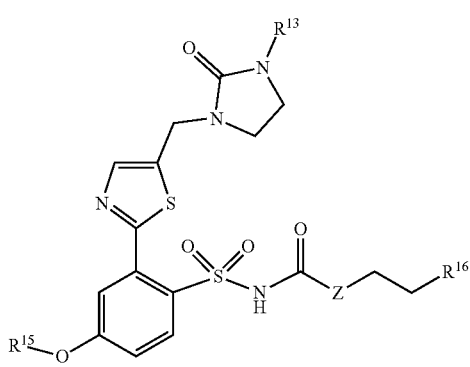

6b

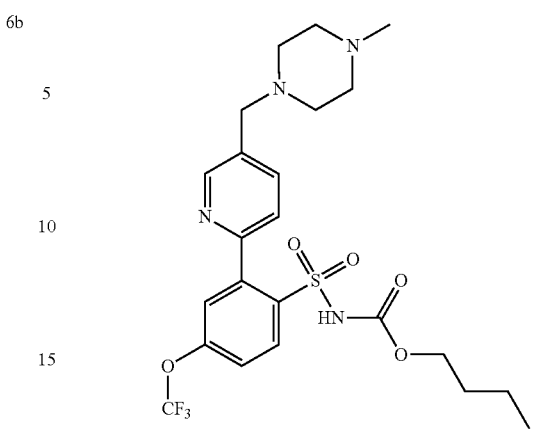

10 wherein:

R[10] and R[11] are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that R[10] and R[11] can also be joined to form a carbocyclic, heterocyclic, aryl or hetoaryl ring;

R[12] is hydrogen, alkyl, alkenyl, alkynyl, aryl, heteroaryl, halo, hydroxy, hydroxyalkyl, alkoxyalkyl, alkoxy, aryloxy, or acylamido;

R[13] is hydrogen, alkyl, aryl or heteroaryl;

R[14] is hydrogen, alkyl, aryl, heteroaryl, acyl, alkoxyacyl, aminoacyl, dialkylaminoacyl, or dialkylaminoacyl; and R[15] is alkyl, aryl, heteroaryl, arylmethyl, heteroarylmethyl, trifluoromethyl or pentafluoroethyl; and R[16] is hydrogen, hydroxy, methoxy, alkoxy, alkyl, alkenyl, alkynyl, aryl, heteroaryl, amino, alkylamino, or di alkylamino.

or a pharmaceutically acceptable salt thereof.

In one embodiment of any of the above embodiments, R[10], R[11] and R[12] are hydrogen. In another embodiment, R[15] is trifluoromethyl. In a further embodiment, R[15] is ethyl. In another embodiment, Z is selected from the group consisting of O and —NH. In a further embodiment, the compound is

7

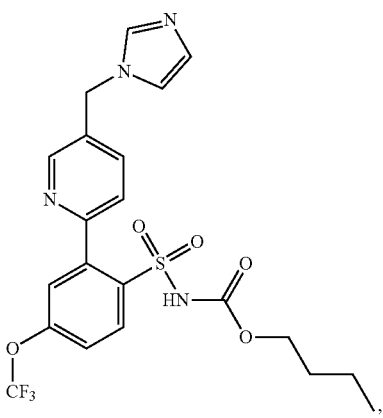

or a pharmaceutically acceptable salt thereof.

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multicyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

The term "alkenyl" refers to a branched or unbranched hydrocarbon having at least one carbon-carbon double bond.

The term "alkynyl" refers to a branched or unbranched hydrocarbon having at least one carbon-carbon triple bond.

The term "carboxy" refers to a —$CO_2H$ group.

The term "hydroxy" refers to an —OH group.

The term "alkoxy" refers a group of the formula R—O— where R is an "alkyl" as defined herein.

The term "carbocycle" refers to a non-aromatic stable 3- to 8-membered carbon ring which may be saturated, mono-unsaturated or poly-unsaturated.

The term "amino" includes primary, secondary or tertiary amino groups.

The term "cyano" refers to the group —CN.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 4 to about 15 members where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, triazolyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "aryloxy" refers to RO—, in which R is aryl, including lower aryl, such as phenyl.

As used herein, "acyl" refers to a —COR group, including for example alkylcarbonyl, cycloalkylcarbonyl, arylcarbonyl, or heteroarylcarbonyls, all of which may be optionally substituted.

As used herein "subject" is an animal, typically a mammal, including human, such as a patient.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, the term "treating" means any manner in which one or more of the symptoms of a disease or disorder are ameliorated or otherwise beneficially altered. Treatment also encompasses any pharmaceutical use of the compositions herein, such as use for treating a disease as provided herein.

As used herein, limiting development of a particular disorder by administration of a particular compound or pharmaceutical composition refers to any lessening, whether permanent or temporary, lasting or transient that can be attributed to or associated with administration of the composition.

Typically, the compounds are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physico-chemical characteristics of the compound, the dosage schedule, and amount administered as well as other factors known to those of skill in the art. Typically a therapeutically effective dosage should produce a serum or plasma concentration of active ingredient of from about 0.1 ng/ml to about 50-100 µg/ml. The pharmaceutical compositions typically should provide a dosage of from about 0.001 mg to about 100 mg of compound per kilogram of body weight per day. Pharmaceutical dosage unit forms are prepared to provide from about 1 mg to about 2,000 mg and preferably from about 10 to about 200 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, intravenously, vaginal, intranasal, buccal, sublingual, rectally, ocularly, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, hydroxyethyl cellulose (HEC), β-cyclodextin, hydroxypropyl β-cyclodextrin, carboxymethyl cellulose colloidal solutions, hydroxyethyl cellulose colloidal solutions polyethylene glycol, glycerine, propylene glycol or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In another embodiment, the compounds are administered in a polymer formulation, including but not limited to Poly-D,L-Lactic-Co-Glycolic Acid (PLGA), poly-lactic acid (PLA), PLA-PLGA co-polymers, polycaprolactone particles, and chitosan nanoparticles.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical compositions of the compounds may be advantageously provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain, along with the active ingredient, a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time-release formulations or coatings.

EXAMPLES

Cardiovascular disease is a major risk factor for the development of neurological disorders. In order to understand the potential of Mas agonists such as those disclosed above as therapeutics for treating cardiovascular disease-related neurological disorders, we assessed activity of Compounds 7 and 10 in a mouse model of trans-aortic constriction (TAC), a model of left-ventricular hypertrophy, which was shown to reduce cognitive function in surgical animals.

All animal survived the surgery and showed no observable adverse events either from the surgery or surgery combined with the Mas agonist treatments (i.e.: compounds 7 and 10). Treatment was initiated one week after TAC surgery (daily SQ injections at a dose of 2 mg/kg/mouse) when aortic constriction was confirmed. The treatment groups (n=12 per groups) included sham surgery controls treated with saline, TAC surgery controls treated with saline, TAC surgery animals treated with A (1-7), TAC surgery animals treated with Compound 7 and TAC surgery animals treated with Compound 10. Blood pressure was measured approximately 5-6 weeks after surgery by tail cuff and unaffected by Compound 7 or Compound 10. A (1-7) treatment in TAC mice significantly reduced diastolic blood pressure and mean atrial pressure. Novel object recognition (NOR) is a test of non-spatial memory. TAC surgery has been shown to decrease NOR performance. The preference of the animal for a novel object over a familiar object exploits the natural tendency of rodents to explore novel objects, was tested 10 weeks after surgery. Completion of the NOR has shown a significant decrease in the cognitive function of mice undergoing TAC and that Compound 7 and Compound 10 significantly increased cognition in this model.

In further studies, measurement of hippocampal cytokine levels in TAC mice treated as disclosed above by multiplexed immunoassay (Meso Scale Discovery) showed treatment with compounds 7 and 10 decreased levels of all cytokines tested: IL-2, IL-10, IL-4, IL-5, IL-6, IL-12p70, IFNγ, KC/GRO, TNFα, and IL-10 (data not shown) compared to saline treated TAC controls. These results support use of the compounds of the disclosure to treat or limit development of neuroinflammation and/or neuroinflammatory diseases.

We claim:
1. A method for increasing cognitive function in a subject having a cardiovascular disease-related neurological disorder, comprising administering to the subject a pharmaceutical composition comprising a pharmaceutically acceptable carrier and an amount effective to increase the subject's cognitive function of a compound selected from compound 7 and compound 10:

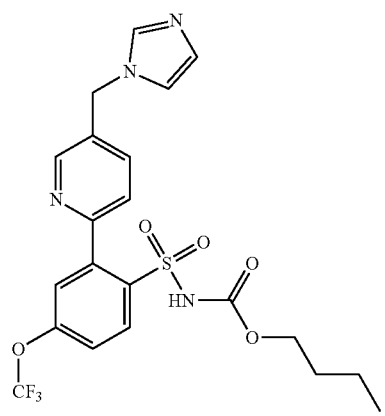

,

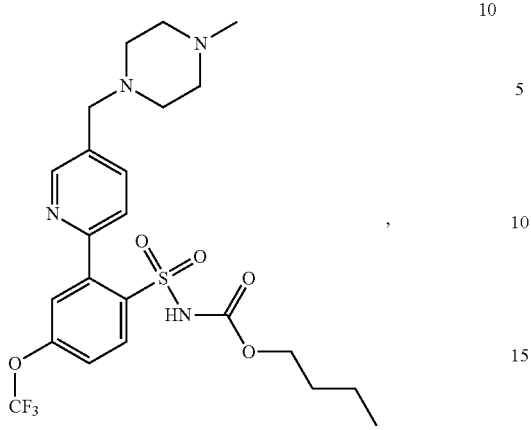

, or a pharmaceutically acceptable salt thereof, and wherein the cardiovascular disease is left-ventricular hypertrophy, and wherein the cardiovascular disease-related neurological disorder is cognitive decline or Alzheimer's disease.

2. The method of claim 1, wherein the cardiovascular disease-related neurological disorder is Alzheimer's.

3. The method of claim 1, wherein the compound is compound 7.

* * * * *